Figure 1:
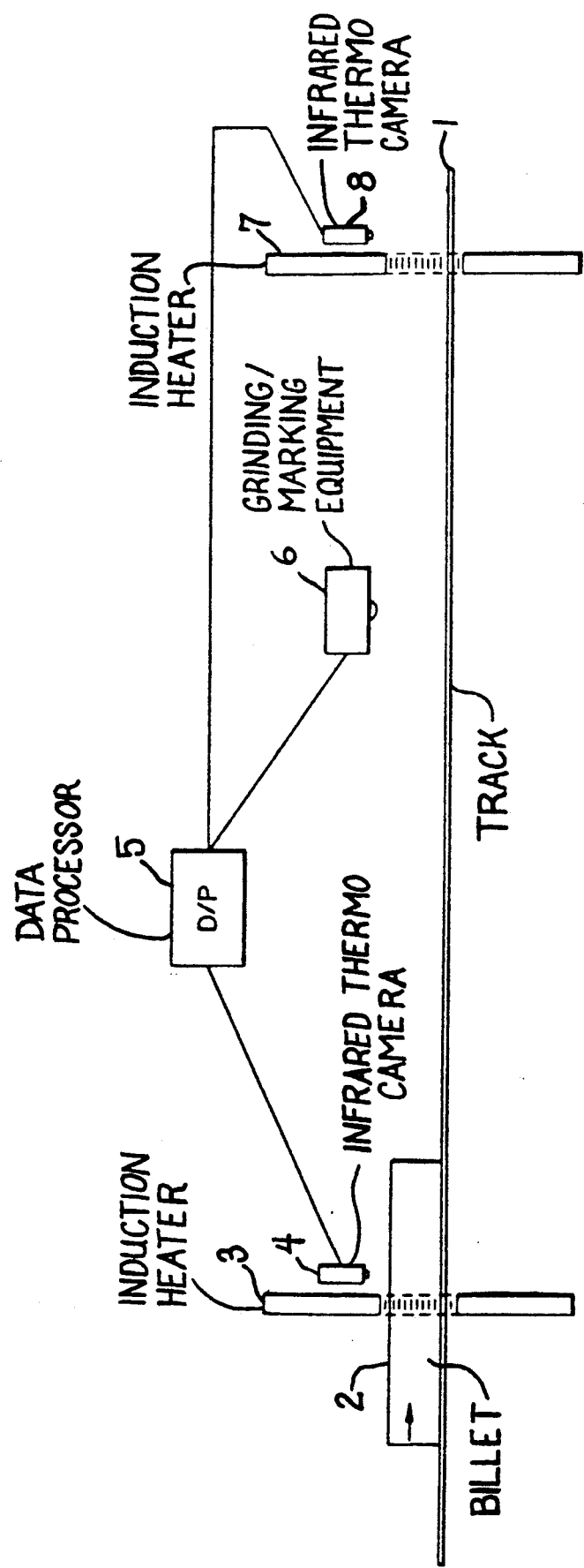

United States Patent [19]

Hovland et al.

[11] Patent Number: 5,069,005
[45] Date of Patent: Dec. 3, 1991

[54] METHOD OF FLAW DETECTION IN BILLETS

[75] Inventors: Heljar Hovland, Asker; Jan Nilsen, Lillesand; Yngve Strom, Osto, all of Norway

[73] Assignee: Elkem Technology a/s, Norway

[21] Appl. No.: 451,756

[22] Filed: Dec. 18, 1989

[30] Foreign Application Priority Data

Jan. 10, 1989 [NO] Norway ................. 890106

[51] Int. Cl.$^5$ ................................ B24B 1/00
[52] U.S. Cl. ........................... 51/322; 374/5; 374/137
[58] Field of Search .............. 374/4, 5, 124, 137; 51/322

[56] References Cited

U.S. PATENT DOCUMENTS

| | | | |
|---|---|---|---|
| Re. 32,166 | 6/1986 | Berge | 374/5 |
| 3,020,745 | 2/1962 | Sielicki | 374/5 |
| 4,109,508 | 8/1978 | Fukuyama | 374/5 |
| 4,480,928 | 11/1984 | Halsor et al. | 374/5 |
| 4,551,030 | 11/1985 | Luukkala et al. | 374/5 |

FOREIGN PATENT DOCUMENTS

| | | |
|---|---|---|
| 50-111953 | 3/1977 | Japan . |
| 834486 | 5/1981 | U.S.S.R. . |
| 857837 | 8/1981 | U.S.S.R. . |
| 890204 | 12/1981 | U.S.S.R. . |
| 1004847 | 3/1983 | U.S.S.R. . |

*Primary Examiner*—Daniel M. Yasich
*Attorney, Agent, or Firm*—Lucas & Just

[57] ABSTRACT

The present invention relates to a method for detecting flaws and surface defects in metallic workpieces, particularly in non-magnetic steel workpieces. The surface of the workpiece is heated by passing the workpiece in its longitudinal direction through an induction coil, scanning the surface of the workpiece with an infrared camera transversely across the surface of the moving workpiece immediately after induction heating and recording a streaked pattern temperature profile in which the streaked pattern repeats itself where there are flaws in the surface. It is used an induction coil with a current frequency which gives a penetration depth of the induced current in the workpiece which is greater than the depth of the flaws which are to be detected. The flaws and surface defects are detected by recording a lower surface temperature than the rest of the surface of the workpiece by scanning the temperature profile immediately after induction heating.

19 Claims, 1 Drawing Sheet

METHOD OF FLAW DETECTION IN BILLETS

This invention relates to a method for flaw detection in metal members such as blooms or billets of steel or aluminium. The method of the present invention is particularly suited for detecting surface flaws in non-magnetic steel.

It is well known that surface flaws occur in formation of steel work pieces such as blooms or billets, and many different methods have been developed in order to detect these surface flaws for the purpose of eliminating them by grinding or the like.

From U.S. Pat. No. Re. 32,166 there is known a method for detection of flaws and surface defects in metallic workpieces where the workpiece is heated by passing it through an induction heater for induction heating with a high frequency current, and where the workpiece is scanned with an infrared camera to determine the temperature profile of the scanned portion of the workpiece immediately after induction heating. The output signal from the infrared camera is used to generate a streaked temperature profile in which the streaked pattern repeats itself where there are flaws in the surface of the metallic workpiece. According to U.S. Pat. No. Re. 32,166 there is found an increase in temperature adjacent surface irregularities, such as cracks. The increase in temperature due to a crack will, when the patterns from repeated temperature scannings are made, form a streaked pattern indicating a longitudinal surface crack in the workpiece. The cracks in the workpiece which do not run at a too steep angle to the longitudinal axis of the workpiece can thus be detected by the method described in U.S. Pat. No. Re. 32,166.

From U.S. Pat. No. 4,109,508 there is known a similar method for detecting surface flaws in metallic workpieces. According to this method the temperature across the workpiece is scanned before and after the workpiece is heated by passing it through a high-frequency induction coil. If the measured increase in temperature due to the induction heating for certain points on the surface of the workpiece exceeds the temperature increase for a crack-free surface, this indicates flaws in the workpiece. Both the method according to U.S. Pat. No. Re. 32,166 and U.S. Pat. No. 4,109,508 are thus based on the fact that a crack is indicated by a higher increase in the surface temperature in the area adjacent the crack than on the rest of the surface of the workpiece, after the surface of the workpiece has been heated by passing it through a high frequency current coil. It has been found that these known methods can be used with good results on magnetic materials such as magnetic steel. However, for non-magnetic material such as non-magnetic stainless steel it has been difficult to obtain detection of flaws by the above mentioned methods.

When the above described known methods are used for detecting flaws in non-magnetic steel, it is found that the increase in surface temperature adjacent a flaw will not be higher than the increase in temperature of the crack-free part of the workpiece. It is believed that the reason for this is the differences in electric resistivity and permeability for magnetic and non-magnetic steels. Thus when using a high frequency current coil with a frequency of 30,000 to 40,000 Hz the penetration depth of the induced current in the workpiece will for magnetic steel normally be substantially lower than the depth of the surface cracks which are to be detected. This low penetration depth of the induced current results in a much higher temperature increase in areas with flaws than in a flaw-free part of the surface.

Due to the differences in electric resistivity and permeability, it would for non-magnetic steels be necessary to increase the frequency of the current coil about 40 times in order to obtain the same low current penetration depth for non-magnetic steels as for magnetic steels. Thus such high frequencies would be necessary that with the present available high frequency induction coils it would neither be technically nor economically viable to use such high frequencies for detection of flaws.

It is therefore an object of the present invention to provide a method for detection of surface flaws in metallic workpieces, particularly in non-magnetic steel workpieces, which will overcome the above mentioned drawbacks of the known methods.

Accordingly, the present invention relates to a method for detecting flaws and surface defects in metallic workpieces, particularly in non-magnetic steel workpieces, where the surface of the workpiece is heated by passing the workpiece in its longitudinal direction through an induction coil, scanning the surface of the workpiece with an infrared camera transversely across the surface of the moving workpiece immediately after induction heating and recording a streaked pattern temperature profile in which the streaked pattern repeats itself where there are flaws in the surface, characterized in that there is used an induction coil with a current frequency which gives a penetration depth of the induced current in the workpiece which is greater than the depth of the flaws which are to be detected. The flaws and suface defects are detected by recording a lower surface temperature than the rest of the surface of the workpiece by scanning the temperature profile immediately after induction heating.

The method of the present invention uses a current frequency which gives a penetration depth of the induced current which exceeds the depth of the flaws when the workpiece is passed through the induction coil. Thus the current will flow down and under flaws in the workpiece. It has surprisingly been found that in the areas of the surface at the edges of a flaw thus will be less heated than the flaw free part of the workpiece. By scanning the temperature profile immediately after the workpiece has left the induction coil, the part of the workpiece having flaws will thus show a lower temperature than the flaw-free part of the workpiece. It is, however, important that the temperature profile is recorded before the temperature has been equalized, and in practice the temperature profile must be scanned less than 0.1 second after the workpiece has left the induction coil. Preferably the temperature profile is recorded less than 0.05 seconds after the workpiece has left the induction coil.

When the method according to the present invention is used for detecting flaws in non-magnetic steel; an induction coil with a frequency of up to 50,000 Hz is used. This is satisfactory for obtaining a safe detection of flaws of normal depth. When the method of the present invention is used for magnetic steel, frequences in the range between 100 Hz and 1000 Hz are used. The frequency needed for a certain material can easily be found determined or by a person skilled in the art based on the known relations between the penetration depth of the current and electric resistivity and permeability.

The invention will now be further described with reference to the accompanying FIG. 1, which shows a schematic of an apparatus which can be used in the present invention.

The apparatus shown on FIG. 1 is in principle identical to the apparatus which is used in the invention of U.S. Pat. No. Re. 32,166 and comprises a track 1, along which a billet 2 is progressing in the direction of the arrow as indicated thereon. The billet passes through an induction heater 3 which operates at a frequency between 100 and 50,000 Hz, depending on the electrical characteristics of the billet.

Downstream the induction heater 3, and positioned immediately after the induction heater 3, is an infrared thermo camera 4 which scans the workpiece and forms a temperature profile. When the temperature across the workpiece is measured a temperature decrease will be found adjacent surface irregularities such as cracks. The temperature profile will form a streaked temperature pattern across the surface and the surface irregularities will be indicated by the fact that the streaked pattern repeats itself. The data obtained from the infrared camera can be recorded as a hard copy, but is preferably fed directly to a data processor 5, which in turn controls downstream marking equipment 6, such as a marking pen or grinding equipment. Since the size, shape and depths of the crack can be found from the temperature profile, the exact grinding necessary to remove the cracks can be established. After the grinding the workpiece can be subjected again to flaw detection apparatus, induction heater 7 and infrared thermo camera 8, to ensure that the correct grinding has been effected.

The above described apparatus was used for detecting flaws in a non-magnetic stainless steel billet having the following chemical compositions:

Max 0.08% C., max 2% Mn, max 0.045% P, max 0.03% S, max 1% Si, 18–20% Cr, 8–10.5% Ni and rest Fe.

It was used an induction coil with a frequency of 40,000 Hz, which gives a current penetration in the steel of 2.2 mm. The temperature profile was recorded 5 mm downstream of the coil. The velocity of the workpiece through the coil was 0.5 m/s. For cracks with a depth of 0.8 mm it was for the above steel found a decreased temperature of 5° C. compared to the temperature of crack-free surface.

What is claimed is:

1. In a method for detecting flaws and surface irregularities in a metal workpiece where the surface of the workpiece is heated by passing it through an induction coil, and immediately downstream of the coil, scanning the workpiece with an infrared camera to determine a temperature profile across the workpiece, and recording a streaked pattern temperature profile in which the streaked pattern repeats itself where there are flaws in the surface of the workpiece, the improvement comprising the steps of using a predetermined current frequency in said induction coil which induces a current in the workpiece, said current penetrating into said workpiece a depth which exceeds the depth of the flaws which are to be detected, thereby producing a lower surface temperature in the surface of the workpiece adjacent the flaws than in the rest of the surface of the workpiece.

2. Method according to claim 1, wherein the temperature is recorded by scanning the temperature profile less than about 0.1 second after the workpiece has passed the induction coil.

3. Method according to claim 2, wherein the temperature is recorded by scanning the temperature profile less than about 0.05 seconds after the workpiece has passed the induction coil.

4. Method according to claim 3, wherein said workpiece is made of non-magnetic steel and said current frequency is up to about 50,000 Hz.

5. Method according to claim 3, wherein said workpiece is made of magnetic steel and said current frequency is between about 100 and about 1000 Hz.

6. In a method for detecting flaws and surface irregularities in a metal workpiece made of magnetic steel having the steps of heating the workpiece by passing the workpiece through an induction coil of a set current frequency to induce a current in said workpiece and heat the surface of the workpiece, scanning the surface of the workpiece with an infrared camera immediately downstream of said coil to determine a temperature profile across the surface of the workpiece, and recording a streaked pattern temperature profile wherein the streaked pattern repeats itself where there are flaws in the surface of the workpiece, the improvement comprising:

(a) employing a predetermined current frequency in said induction coil of between about 100 and about 1000 Hz such that the induced current in said workpiece penetrates into said workpiece a depth that exceeds the depth of said flaws and surface irregularities in said workpiece; and (b) scanning said workpiece less than about 0.05 seconds after said workpiece has passed said induction coil.

7. A method for detecting surface flaws in a metallic workpiece, said surface flaws extending a depth below the surface of said workpiece, comprising:

(a) heating said workpiece by passing said workpiece through a first induction heater, said induction heater operating at a predetermined current frequency which induces a current in said workpiece such that said current in said workpiece penetrates said workpiece a depth that exceeds the depth of said surface flaws;

(b) scanning said workpiece with a first infrared camera immediately after said heating step to obtain a temperature profile of said workpiece wherein the surface of said workpiece adjacent to said flaws has a lower temperature than the rest of the surface of said workpiece;

(c) generating an output signal in said first infrared camera corresponding to said temperature profile; and (d) feeding said output signal to a data processor which controls a grinding apparatus for automatically grinding said workpiece in accordance with said temperature profile.

8. The method of claim 7 further comprising the steps of:

(a) reheating said workpiece by passing said workpiece through a second induction heater at a current frequency which induces a current in said workpiece such that said current in said workpiece exceeds the depth of said surface flaw and (b) rescanning said workpiece with a second infrared camera immediately after reheating said workpiece to determine a new temperature profile of said workpiece and insure correct grinding had been effected.

9. The method of claim 7 wherein said scanning step takes place within less than about 0.1 second after said heating step.

10. The method of claim 7 wherein said scanning step takes place within less than about 0.05 seconds after said heating step.

11. The method of claim 7 wherein said workpiece is a billet of non-magnetic steel and said current frequency is up to about 50,000 Hz.

12. The method of claim 7 wherein said workpiece is a billet of magnetic steel and said current frequency is between about 100 and about 1000 Hz.

13. The method of claim 7 wherein said current frequency is between about 100 and about 50,000 Hz.

14. The method of claim 9 wherein said workpiece is a billet of non-magnetic steel and said current frequency is up to about 50,000 Hz.

15. The method of claim 9 wherein said workpiece is a billet of magnetic steel and said current frequency is between about 100 and about 1000 Hz.

16. The method of claim 9 wherein said current frequency is between about 100 and about 50,000 Hz.

17. The method of claim 10 wherein said workpiece is a billet of non-magnetic steel and said current frequency is up to about 50,000 Hz.

18. The method of claim 10 wherein said workpiece is a billet of magnetic steel and said current frequency is between about 100 and about 1000 Hz.

19. The method of claim 10 wherein said current frequency is between about 100 and about 50,000 Hz.

* * * * *